Figure 1:
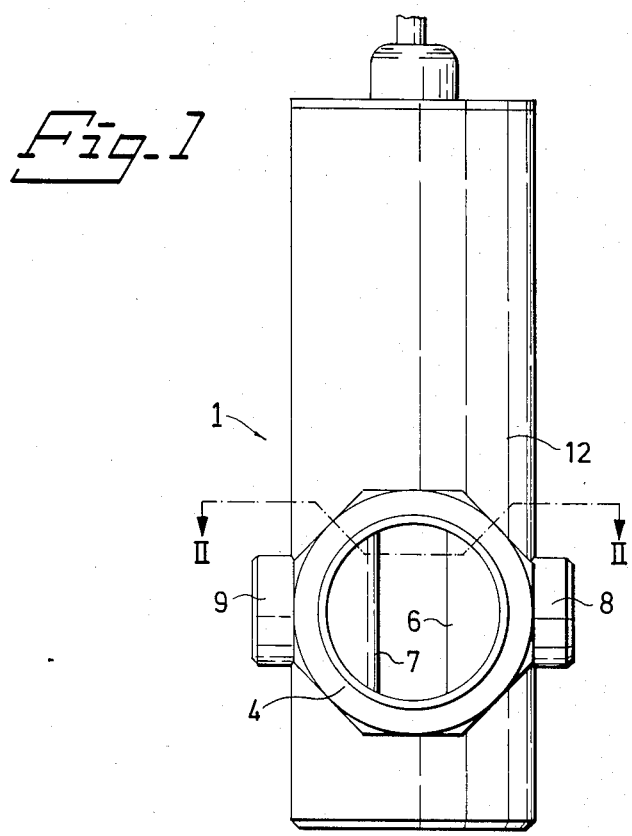

United States Patent [19]

Jelvestam et al.

[11] Patent Number: 4,492,868

[45] Date of Patent: Jan. 8, 1985

[54] DEVICE FOR MEASURING CONCENTRATION OF PARTICLES CONVEYED BY A LIQUID

[76] Inventors: Roland E. Jelvestam, Björnidegränd 29, S-163 64 Vällingby; Pär-Hålan Bergström, Vassvägen 5H, S-141 39 Huddinge, both of Sweden

[21] Appl. No.: 439,224

[22] Filed: Nov. 4, 1982

[30] Foreign Application Priority Data

| Nov. 25, 1981 [SE] | Sweden | 8107026 |
| Nov. 25, 1981 [SE] | Sweden | 8107027 |

[51] Int. Cl.³ .................... G01J 5/54; G01N 21/84
[52] U.S. Cl. ........................ 250/345; 250/343; 356/441
[58] Field of Search .............. 250/343, 345, 432 R, 250/359.1, 358.1; 356/442, 441

[56] References Cited

U.S. PATENT DOCUMENTS 3,920,334 11/1975 Steichen et al. ............ 356/73
4,072,424 2/1978 McMullan et al. ............ 356/442
4,243,883 1/1981 Schwarzmann ............ 250/343

OTHER PUBLICATIONS

Edward S. Posgate "A Turbidity/Suspended Solids Monitor" *American Laboratory* vol. 7, No. 12, (Dec. 1975) pp. 67–73.

*Primary Examiner*—Janice A. Howell
*Assistant Examiner*—Constantine Hannaher
*Attorney, Agent, or Firm*—Ladas & Parry

[57] ABSTRACT

A measuring device for measuring the concentration of particles in a liquid advanced through a tube (2) includes a transducer where the tube in a measuring zone has an area change implemented such that the pipe wall is kept clean from deposits. Probes (8, 9) are inserted in the tube wall (6, 7) so that the measuring surfaces of the probes are in contact with the liquid and form a part of the tube wall. The measuring device is compensated for temperature by means of a reference apparatus (13, 14) coacting with said probes electrically and mechanically.

14 Claims, 4 Drawing Figures

DEVICE FOR MEASURING CONCENTRATION OF PARTICLES CONVEYED BY A LIQUID

DESCRIPTION

1. Technical Field

The present invention relates to a measuring device for measuring the concentration of particles conveyed by a liquid through a conduit. Measuring probes are thereby arranged in the wall of the conduit and in contact with the liquid.

2. Background Art

In measuring the concentration of particles in substantially stationary liquids it is known, for example in conjunction with purification of municipal and industrial waste water, to utilize photometric measurement with the aid of pulsed infrared (IR) light, as will be seen from the Swedish Pat. No. 382 116.

This method of the prior art has its limitations, and is primarily applicable to stationary liquids at substantially constant temperature. With varying temperature the method would give rise to substantial measuring error. This method is furthermore burdened with other disadvantages, such as the need of cleaning the measuring probes from particle deposits after a short time in use, and that considerable modification and supplementation must be resorted to for the apparatus used in the method to be applied to particle measurement in flowing liquids, as in pulp conveyors in the cellulose industry.

DISCLOSURE OF INVENTION

The above mentioned drawbacks and difficulties are avoided by the present invention, such as it is defined by the characterizing portion of the following claim 1.

Using the present measuring device, it has now been possible to show that measuring with measuring probes of the kind in question may very well be carried out on particle-containing liquid which is advanced through a conduit. Those skilled in the art have previously alleged that measuring with the aid of IR probes e.g. measuring the fibre concentration in advancing paper pulp, would be impossible or at least required continuously repeated cleaning of the measuring probes. This is however an opinion which is completely confounded by the present invention. By changing the cross-sectional area of the tube or conduit it has been found that the probe surfaces facing towards the liquid are automatically kept clean.

With measuring probes connected to an electronic circuit, which is also connected to a reference apparatus comprising reference measuring means, which are in heatconductive contact with the tube or conduit for advancing the liquid, the device in accordance with the invention has also obviated previous problems, which were difficult to solve, in respect of the instability of measuring circuits for measurements in liquids of the kind given. This reference apparatus has a function tied in with the configuration of the measuring zone and is enclosed by a casing surrounding the liquid-advancing tube and the measuring probes.

The measuring device is accordance with invention has its field of use within the process industry as well as water supply and sewage system. The device is intended for accurate concentration measurement, e.g. within the paper and cellulose industry, where measurement can be made in front of pressure screens and vortex cleaners, on the stock before the head box on a paper making machine, and in white water for both dilution and fibre recovery. In the area of water supply and sewage, the device is utilizable for sludge content and turbidity measurement and measurement of the content of suspended material, e.g. in reject water from dewatering centrifuges or other mechanical dewatering machines.

The measuring principle is based on the ability of particles to absorb and reflect light.

In order to achieve the greatest possible flexibility, a portion of the electronics have been mounted at the transducer. Measuring is done with IR light over a measuring distance of 20 mm. The IR light is pulsed with very short pulses and has very great light intensity, which is possible due to pulsing with extremely short pulses and long intervals therebetween. With great light intensity there is obtained the advantage that different measuring ranges can be utilized, by simple recircuiting of an amplifier incorporated in the electronic circuit. Since the light yield from an IR diode is heavily dependent on temperature, this is compensated via a separate reference system in the transducer. This also compensates for the drift in other components and for possible incident random light.

The measuring signal from the transducer comprises a pulse, the amplitude of which is proportional to the concentration. This pulse can be converted to a direct voltage in a sampling and holding circuit, connected at the same time to the integrating time. This integrating time has a fixed rate about its measuring value, and an adjustable rate for damping any great variations in the concentration.

After the samping the holding circuit the signal may be taken to means for providing a maximum and minimum setting, directly or via a logarithmic amplifier. The amplification of the output step can be changed by means of a switch. A digital measuring value indicator displays 0–100% of a selected range, independent of what output signal is selected.

PREFERRED EMBODIMENT

Figure 2:
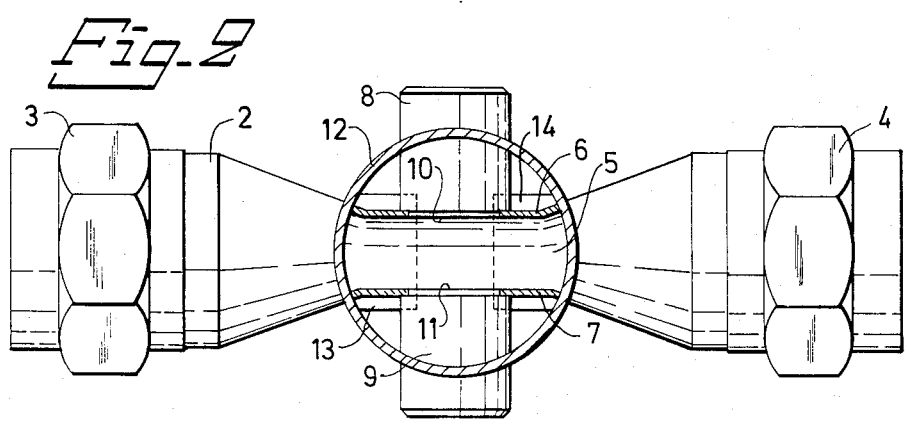
Figure 3:
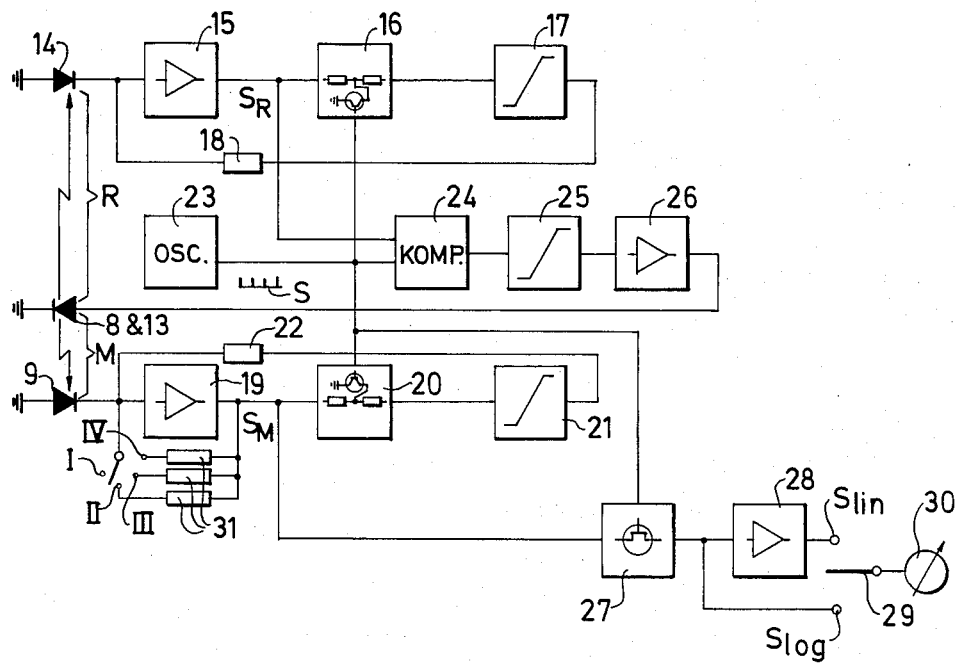
Figure 4:
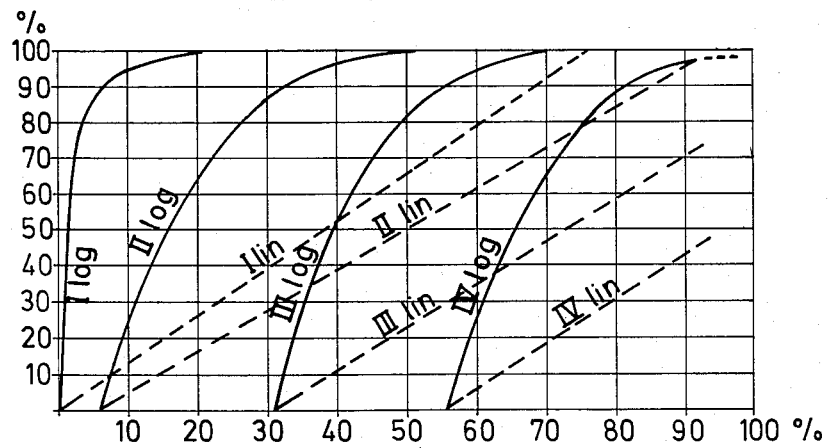

The measuring device is accordance with the invention will now be described in detail, in conjunction with a preferred embodiment and with reference to the attached drawings, where FIG. 1 is a front view of the transducer for a preferred embodiment of the invention, seen from the upstream side of the liquid travel direction, FIG. 2 is a section II—II according to FIG. 1, FIG. 3 is a block diagram with a preferred electrical circuitry for connecting the emitters and detectors in the transducer to a measuring value unit, and FIG. 4 illustrates graphs for the exemplification of possible differentiated measuring ranges which may be switched in.

The measuring device in accordance with the invention includes a transducer 1 which, in a preferred embodiment according to FIGS. 1 and 2, includes a tube 2 for advancing the particle-containing liquid on which measurements are to be taken. The tube 2 is provided with connection means 3, 4 for coupling into a conduit (not shown). In the measuring zone, the cross-sectional area of the tube 2 is changed in its configuration, but preferably has the same magnitude. Accordingly, the cross-sectional area of the tube 2 in the preferred embodiment goes from a normal, circular cross-sectional at the connection means 3, 4 to a substantially rectangular cross-section 5, as will best be seen from FIG. 1. This transition from circular to rectangular cross-section is continuous and can be provided in several ways, but most simply by compressing an initially circular tube.

There are openings made in the opposing walls 6, 7 of the tube 2 within the rectangular area 5 for mounting measuring probes 8, 9. The probes 8, 9 completely fill out the openings in the tube walls 6, 7 and their probing surfaces 10, 11 facing towards the advanced liquid are substantially in the same plane as the inner surface of the tube walls 6, 7.

The measuring zone with the rectangular tube area 5 and the probes 8, 9 is surrounded by a casing 12. This casing 12 is preferably tubular and has a longitudinal axis extending perpendicular to that of the tube 2 as well as that formed by the probes 8, 9. Openings are made in the casing 12 for the insertion and inspection of the probes 8, 9 which may project out past the casing 12 as shown.

The casing 12 further encloses a reference apparatus 13, 14 comprising measuring means corresponding to the measuring probes 8, 9 but not measuring the liquid as the probes 8, 9 do, instead they measure over an obstacle-free path within the casing. The reference apparatus 13, 14 is in heat-conductive contact with the tube 2, and may be mounted under (as indicated in FIG. 2) or preferably over the tube 2.

The casing 12 also encloses at least a portion of the electronic circuits used for processing the signals obtained from the probes 8, 9 and reference apparatus 13, 14. The probes, as well as the reference apparatus, are to advantage of the IR type, even if other types such as those working with visible light or supersonic sound may be utilized in realizing the present invention. A preferred embodiment of the electronic circuit will now be described in the following with reference to FIG. 3.

It will be seen the block diagram in FIG. 3 that the measuring probes 8, 9 and reference apparatus 13, 14 comprise IR means, more specificlly, IR diodes may be used to advantage. The emitter of the probes is furthermore depicted as a means common with the reference apparatus emitter 13. Accordingly, an IR diode 8, 13 may be used as a common emitter over the measuring distance M as well as the reference distance R, the different paths of light M and R departing from fibre optics connected to the diodes 8, 13, for example. Another practicable solution is to connect two exactly alike IR diodes 8 and 13 in series, these thus constituting the emitter of the measuring distance M and the emitter of the reference distance R.

The detector 9 of the measuring probes is, like the detector 14 of the reference apparatus, a separate photodiode. Both these photodiodes are of the same type and are connected to each other by temperature-compensating circuit 15-18 and 19-22, respectively, of exactly the same implementation. The output of the respective photo diode 9, 14 is thus connected to an amplifier 15, 19 which feeds an integrator 17, 20 via a holding circuit 16, 21. The integrated signal is looped back via a resistor 18, 22 to the input of the amplifier 15, 19. A diode is relatively dependent on temperature, but the compensating circuits 15-18 and 19-22 provide a stabilizing function, so that the output signal level from the respective amplifier 15, 19 is kept constant, irrespective of temperature variations which may occur round the detectors 9, 14, such as in the liquid where the particle concentration is to be measured, in the air in the obstacle-free reference path and in the tube in thermic contact with the reference apparatus. A stabilizing function is also attained with these compensating circuits 15-18, 19-22 for possible random light which can be incident on the detector 9, 14. Thus, each more slow output signal change from the detectors 9, 14 will be smoothed out so that a stable reference level is obtained on the output of amplifiers 15, 19.

The signal emitter or emitters 8, 13 arranged for the measuring and reference signals is or are fed from an oscillators 23. This oscillator generates a pulse signal S with very short-duration pulses and relatively long intervals between the pulses. This allows great light intensity to be obtained without the IR diodes 8, 13 being damaged due to self-heating. Since the emitter 8, 13 similarly consists of a diode it is also sensitive to temperature variations. These variations are compensated by a circuit 24-26 comprising a comparator 24 followed by an integrator 25 and a power amplification step 26. The comparator 24 is fed with the pulse signal S from the oscillator 23 and the output signal $S_R$ from the reference apparatus amplifier 15. This output signal $S_R$ is similarly a pulse signal and varies in direct response to the magnitude of the light pulses sent by the emitter 8, 13 over the reference distance R. The magnitude of the light pulses sent by the emitter 8, 13 are regulated by the comparator 24 and the power amplification step 26 so that the pulse signals S and $S_R$ will be equally as great. There are thus obtained light pulses with constant value independent of temperature variations in the emitter 8, 13. Even if the emitter comprises two individual diodes 8 and 13, as described above, light pulses are obtained from each of the diodes 8 and 13 having constant value, since both diodes 8 and 13 are electrically connected in series and mechanically connected to the same base, thereby being affected by the same temperature variations.

The light pulses of constant value sent by the emitter 8, 13 are also caught by the detector 9 after having passed the measuring distance M, i.e. after having passed through the liquid with the particles therein. Since the particle concentration varies, the light pulses caught by the detector 9 will also vary due to the light absorption properties of the particles. A result of this will be that the output signal $S_M$ on the amplifier 19 of the measuring detector 9 varies in response to the particle concentration in the liquid.

In order that the temperature-compensating circuits 15-18, 19-22 of the detectors 9, 14 shall not be affected by the useful signals $S_R$ and $S_M$, there is a holding circuit 16, 20 connected between the amplifier 15, 19 and the integrator 17, 21 in each of the temperature-compensating circuits 15-18, 19-22. This holding circuit 16, 20 is controlled by the output signal S from the oscillator 23 so that the useful signals $S_R$, $S_M$ are grounded when they occur at the holding circuit 16, 20. A contributing reason as to why the useful signals $S_R$, $S_M$ are not feed-back coupled to the inputs of the amplifiers 15, 19 is that the temperature-compensating circuits 15-18, 19-22 are slow in function.

The useful signal $S_M$ taken off from the output of the amplifier 19 associated with the measuring detector 9 thus constitutes an accurate measure of the concentration of particles in the liquid advanced through the tube 2 (see FIG. 2). This signal $S_M$ is consequently utilizable for different purposes in processes of different kinds.

For measuring purposes, but also for other applications, it may be desirable to obtain a smoothly proceeding output signal instead of the pulsed output signal $S_M$. By feeding the output signal $S_M$ to a sampling and holding circuit 27, controlled by the signals S of the oscillator 23, there is obtained a logarithmically varying signal $S_{log}$. If a linearly varying signal $S_{lin}$ is desired, the signal $S_{log}$ obtained from the sampling and holding circuit 27 is fed to a logarithmic amplifier 28. Using a switch 29, a meter 30 can be optionally fed with the signal $S_{log}$ or the signal $S_{lin}$.

The sampling and holding circuit 27 may be a field effect transistor (FET) and the meter 30 may be a digital indicator. The output signal from the amplifier of measuring detector 9 can be optionally feed-back coupled to its input via different resistors 31 so that different measuring ranges I–IV are obtained. For example, four different measuring ranges can be arranged. In FIG. 4 there is shown by means of graphs how the measuring range can be displaced both for the logarithmic signals $S_{log}$ and the linear signal $S_{lin}$ corresponding thereto. Here to range I represents a maximum resistor value coupled into the feed-back loop of the amplifier 17, while the range IV corresponds to a direct looping of the output signal $S_M$ to the input of the amplifier 19.

As will be seen from the description above, there is only intended here a preferred embodiment of the invention which can consequently be modified in different ways without departing from the inventive concept. For example, the cross-sectional area of the tube 2 may be changed into some configuration other than rectangular, or it may be larger than the conduit area. The cross-sectional area can also be changed by arranging an insert in an expanded portion of the tube or by arranging an implementation of the tube wall, which affects the advance of liquid. In respect of the measuring probes and reference apparatus, it has already been stated that these are not limited to the use of IR light. The electronic circuit for the IR components can also be modified in different ways without departing from the inventive concept. For example, the circuit may be formed with switching means for studying only a portion of each graph, e.g. the interval 60–70% of the total measuring range. It is further possible to introduce control means for setting the integration time so that steady indication is obtained on the meter 30.

From what has been said above it will be seen that the invention may not be regarded as limited to the preferred embodiment described above and shown on the drawings, and it may be the subject of different modifications within the scope of what is disclosed in the following claims.

We claim:

1. A measuring device for measuring the concentration of particles conveyed by a liquid through a tube and including measuring probes and a reference apparatus, each one of said measuring probes and reference apparatus including an emitter and a detector, comprising said emitter and said detector of the measuring probes are disposed in the wall of the tube axially in register with each other on either side of the liquid advanced through the tube and said emitter and detector of the reference apparatus are arranged on either side of a reference path being free from liquid and are of the IR type, said emitters being fed from a common source sending pulsed energy to the emitters, said energy having short energy pulses with relatively long time intervals between said pulses, said pulse being of a shorter duration than that of square wave pulses, and said reference apparatus is involved in an electronic circuit being temperature-compensated.

2. Measuring device as claimed in claim 1, characterized in that the cross-sectional area of the tube at the probes differing in configuration and/or size in comparison with the cross-sectional area of the tube before and after the probes.

3. Measuring device as claimed in claim 1, characterized in that the cross-sectional area of the tube at the measuring probes is substantially rectangular, whereas the cross-sectional are before and after said probes is circular while retaining substantially constant flow-through area, the tube at the probes being surrounded by an outer casing for enclosing the probes and reference apparatus, so that the reference emitter and reference detector are adapted axially in register with each other and in heat-transferring contact with the tube.

4. Measuring device as claimed in claim 1, characterized in that the emitters of the probes and reference apparatus is a common means adapted for energizing the detector of the measuring probes via the liquid with particles, and the detector of the reference apparatus over said liquid free path.

5. A measuring device according to claim 1 which comprises the detector of said measuring probes and the detector of said reference apparatus each having a temperature-compensating circuit associated therewith, each of said temperature-compensating circuits including an amplifier connected to its respective detector,
   comparator adapted for comparing the pulse energy sent from the source with pulse energy generated by the detector of the reference apparatus after amplification in its temperature—compensating circuit,
   an integrator adapted for receiving and integrating the output of said comparator, and
   a power amplifying circuit adapted for receiving and amplifying the output signal of said integrator, the output signal of which is fed to said emitters,
   the amplifier of said temperature—compensating circuit associated with the detector of the measuring probe providing a measuring signal at its output denoting the concentration of said particles.

6. Measuring device as claimed in any of the claim 5, characterized in that the amplifier in the temperature-compensating circuit for the detector of the measuring probes has different looping steps which may be coupled in for subdividing the measuring range for different concentrations of particles.

7. A measuring device as claimed in claim 5 which further comprises:
   a sample and holding circuit having a control input connected to said source and being adapted to receive the measuring signal from the amplifier of the temperature—compensating circuit of the detector of said measuring probes, the measuring values obtained from the sampling and holding circuit varying logarithmically with the concentration of particles.

8. Measuring device as claimed in claim 7, characterized by a logarithmic amplifier circuit which is connectable to the sampling and holding circuit for obtaining a linearly varying measuring value in response to the concentration of particles.

9. A measuring device for measuring the concentration of particles conveyed by liquid through a tube, measuring probes being adapted in the tube wall so as to be in contact with the liquid at a section of said tube having a mainly rectangular cross-sectional area said measuring probes include an emitter and a detector disposed in register with each other on either side of the tube through-flow area for the liquid, comprising said cross-sectional area of the tube at the measuring probes having mainly the same size in comparison with the cross-sectional area of the before and after the probes, and in that section of the tube at the measuring probes is surrounded by an outer casing for enclosing the probes and a reference apparatus, said measuring probes include an IR emitter and IR detector, fed with pulsed energy, said reference apparatus has corresponding IR emitter and IR detector, fed with pulsed energy from a source which is common to the measuring probes and the reference apparatus, and the detector of said measuring pulses and the detector of said reference apparatus each having a temperature compensating circuit associated therewith, each of said temperature compensating circuits including an amplifier connected to its respective detector, a comparator adapted for comparing the pulsed energy sent from the source with pulse energy generated, by the detector of the reference apparatus after amplification in its temperature—compensating circuit, an integrator adapted for receiving and integrating the output signal of said comparator, a power amplifying circuit adapted for receiving and for amplifying the output signal of said integrator, the output signal of which is fed to said emitters, the amplifier of said temperature—compensating circuit associated with the detector of the measuring probes providing a measuring signal at its output denoting the concentration of said particles.

10. Measuring device as claimed in claim 9, characterized in that the cross-sectional area of the tube goes continuously from a circular cross-section to said rectangular cross-section.

11. Measuring device as claimed in claim 9, characterized in that the casing is tubular with a circular cross-section, and with a longitudinal axis which is perpendicular to the tube for advancing the liquid and also to the longitudinal axis of the measuring probes said measuring probes being removable from the outside of the casing.

12. Measuring device as claimed in claim 9, characterized in that each measuring probe has a surface in contact with the liquid, said surface forming an entirety with the inner surface of the tube.

13. Measuring device as claimed in claim 9, characterized in that the probes and reference apparatus are connected to a temperature-compensated electronic circuit for correct digital display of the measuring value obtained in respect of the particle concentration in the liquid.

14. Measuring device as claimed in claim 9, characterized in that the emitters of the probes and reference apparatus is a common means adapted for energizing the detector of the measuring probes via the liquid with the particles and the detector of the reference apparatus over a reference path.

* * * * *